(12) United States Patent
Alchas

(10) Patent No.: US 7,250,036 B2
(45) Date of Patent: *Jul. 31, 2007

(54) INTRADERMAL SYRINGE AND NEEDLE ASSEMBLY

(75) Inventor: Paul G. Alchas, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/463,677

(22) Filed: Aug. 10, 2006

(65) Prior Publication Data

US 2007/0021719 A1 Jan. 25, 2007

Related U.S. Application Data

(63) Continuation of application No. 10/798,594, filed on Mar. 11, 2004, now Pat. No. 7,108,679.

(51) Int. Cl.
*A61M 5/00* (2006.01)

(52) U.S. Cl. ............... 604/117; 604/110; 604/181; 604/187; 604/272

(58) Field of Classification Search .......... 604/115–117, 604/110, 181, 187, 272, 164.08, 264, 196, 604/274; 141/18, 21, 25
See application file for complete search history.

(56) References Cited

U.S. PATENT DOCUMENTS

| 7,108,679 B2 * | 9/2006 | Alchas | 604/117 |
| 2002/0068909 A1 * | 6/2002 | Alchas et al. | 604/198 |

\* cited by examiner

*Primary Examiner*—Kevin C. Sirmons
*Assistant Examiner*—Catherine N. Witczak
(74) *Attorney, Agent, or Firm*—Robert E. West

(57) ABSTRACT

A method for using a needle assembly for an intradermal injection, and a drug delivery device is provided, which includes a needle cannula and a limiter surrounding the needle cannula and includes a skin engaging surface on the limiter. The limiter is moveable from a first position in which an elongate portion of the needle cannula is exposed for access to a medication vial, to a locked second position in which the limiter is not movable from the second position to the first position. In the second position, the needle tip extends beyond the skin engaging surface a distance of about 3 mm or less.

27 Claims, 5 Drawing Sheets

INTRADERMAL SYRINGE AND NEEDLE ASSEMBLY

CROSS REFERENCE TO RELATED APPLICATIONS

The present application is a continuation of U.S. patent application Ser. No. 10/798,594 filed on Mar. 11, 2004 now U.S. Pat. No. 7,108,679.

BACKGROUND OF THE INVENTION

1. Field of the Invention

The present invention relates to a delivery device for injecting drugs, vaccines, and the like into the intradermal region of the skin.

2. Description of Related Art

There are several injection techniques and devices known in the art. Based on the drug substance being injected, one technique and device may provide for a more efficacious delivery and uptake of the particular drug substance. One technique and device delivers a drug substance intramuscularly using a hypodermic needle that penetrates through a patient's skin and into muscle tissue.

Another technique and device delivers a drug substance into the subcutaneous region of the skin. It is possible that the same device may be used to delivery an intramuscular and a subcutaneous injection, with the health care provider controlling the depth of the injection.

Techniques and devices are also known for administering an injection into the intradermal (intradermal) region of the skin. One technique, commonly referred to as the Mantoux technique, uses a "standard" syringe, i.e., a syringe typically used to administer intramuscular or subcutaneous injections,. The health care provider administering the injection follows a specific procedure that requires a somewhat precise orientation of the syringe with regard to the patient's skin as the injection is administered. The health care provider must also attempt to precisely control the penetration depth of the needle into the patient's skin to ensure that it does not penetrate beyond the intradermal region. Such a technique is complicated, difficult to administer, and often may only be administered by an experienced health care professional.

Devices have been proposed for providing intradermal injections which include shortened fine gauge needles compared to conventional needle sizes. The smaller needles are not intended to penetrate beyond the dermis layer of the skin. Such devices are shown in U.S. Pat. No. 5,527,288 to Gross et al., U.S. Pat. No. 4,886,499 to Cirelli et al., and U.S. Pat. No. 5,328,483 to Jacoby. The proposed devices, however are not without shortcomings and drawbacks.

For example, the devices shown in U.S. Pat. Nos. 5,527,288 and 4,886,499 are highly specialized injectors. The designs for these injectors include relatively complex arrangements of components that cannot be economically manufactured on a mass production scale. Therefore, such devices have limited applicability and use.

For many drug substances, it may be desirable to fill the delivery device at the point of, and immediately prior to use. In this situation, the delivery device is normally filled from a multi-dose vial. A multi-dose vial may be more economical and it enables the user to fill the delivery device with the specific dose required. The multi-dose vial may be pre-filled with a liquid substance or with a dry substance. For example, it is now conventional to reduce certain drugs to a dry or powdered form to increase the shelf life of drugs and reduce inventory space. Multi-dose vials are typically sealed with an elastomeric stopper or septum. A needle on the delivery device may be used to pierce the stopper or septum and draw the drug substance from the vial into the delivery device, typically a syringe. The drug substance may then be administered using the delivery device, which is discarded after use, and the unit-dose vial may be stored for further use.

As advances in understanding the delivery of drug proceeds, the use of intradermal delivery systems is expected to increase. Use of a "standard" length needle to deliver a drug substance intradermally has its shortcomings, come of which are identified above. It is not possible to use a delivery device having a needle length suited for intradermal injection to aspirate a syringe with drug substance from a multi-use vial. Thus, there are shortcomings in the prior art that prevent administering an intradermal injection using a "standard" length needle and a multi-use vial. It would be advantageous to have a drug delivery device capable of accessing substances stored in multi-dose vials and delivering such substances into the intradermal region of the skin without encountering the shortcomings described above.

FIG. 1 shows an intradermal injection device 101 comprising a syringe 114 having a syringe body 116 that defines a reservoir 118 within which a drug substance may be held, a plunger 120 disposed in the syringe body 116 and having a flange 122 at a distal end thereof and a stopper 124 at the opposed proximal end thereof, and a needle assembly 102 secured to a distal end of the syringe body 116. An exemplary needle assembly 102 of the type depicted in FIG. 1 is disclosed in U.S. Pat. No. 6,494,865 to Alchas, the entire contents of which is incorporated by reference herein. The needle assembly 102 is specifically designed for making intradermal injections. The needle assembly 102 may carry a needle cannula 104 having a needle tip 106 at a distal end thereof. Alternatively, the needle cannula 104 may be secured directly to the syringe body 116. The needle assembly 102 also includes a penetration limiter 108 having a hub portion 109 that may be secured to the syringe body 116, and a limiter portion 111 that defines a generally flat skin engaging surface 110 at a distal end of the limiter 108. The limiter 108, which generally surrounds the proximal end of the needle 104, permits a certain predetermined length of the needle cannula 104, including the needle tip 106, to protrude beyond the skin engaging surface 110 so that the distance between the needle tip 106 and skin engaging surface 110 limits penetration of the needle tip 106 into the intradermal space of the patient's skin. Preferably, the needle tip 106 of the needle cannula 104 extends beyond the skin engaging surface 110 a distance ranging from approximately 0.5 mm to 3 mm. The needle cannula 104 and skin engaging surface 110 are also arranged with respect to each other in a generally perpendicular relationship that serves to ensure a generally perpendicular relationship between the needle cannula 104 and the patient's skin; such an angular relationship being preferred when making intradermal injections. The skin engaging surface 110 engages the surface of the skin of a patient and limits the penetration depth of the needle tip 106 into the patient's skin. The needle assembly 102 is secured to the syringe 114 via the hub portion 109, which may be fixedly secured to the syringe body 116, or the hub portion 109 may be secured by a Luer fit or equivalent attachment method.

Referring now to FIG. 2, a conventional syringe 114 being filled from a multi-use vial 126 is shown. The vial 126 includes an open end, a rim surrounding the open end and a reduced diameter neck portion adjacent the rim. The vial 124 is typically sealed with an elastomeric septum 128 which includes a portion inserted into the neck of the vial 126 and a planar rim portion which overlies the vial rim. The septum 128 is normally secured to the vial rim with an aluminum collar 130. In FIG. 2, a conventional syringe 114 is being used to access a drug substance contained within the vial 126. The needle 104 in this case is sufficiently long to penetrate the septum 128 to access the drug substance contained in the vial 126.

As may be appreciated from FIGS. 1 and 2, it is not possible, using a device having a stationary limiter, to fill a reservoir from a conventional vial. The distance d is too short to adequately penetrate the depth of the septum and access the substance contained in the vial. The present invention allows for access to a substance contained in a conventional vial by an intradermal needle device or assembly. As a result, there is no need to pre-fill an intradermal device of the present invention prior to use. Thus, standard methods for preserving the therapeutic and/or diagnostic substances, such as maintaining them in liquid or powder form in conventional vials for future use, may be used with the intradermal devices of the present invention. Furthermore, using the intradermal devices of the present invention, it is possible to use conventional, inexpensive delivery devices such as plastic syringes, in conjunction with the intradermal devices, which are often not appropriate for use as pre-filled devices.

In light of the above, there is a present need for a drug delivery device intradermal that enables a user to fill the intradermal device with a drug substance at the time of use by aspiration from a multi-dose vial, and to administer an injection into the intradermal region of the skin easily and repeatedly and without relying on the experience of the health care professional administering the injection.

SUMMARY OF THE INVENTION

The present invention provides a drug delivery device that overcomes the above-described shortcomings of the prior art. In an embodiment of the present invention, intradermal the drug delivery device, also referred to herein as an intradermal injection device, comprises a syringe having a needle cannula and a limiter that is movable with respect to the forward tip of the needle cannula between a first position in which a length of the needle cannula is exposed that is sufficient to enable aspiration of a drug substance from a multi-dose vial into the syringe, and a second position in which a length of the needle cannula is exposed that is preferably approximately equal to or less than 3 mm, when measured from the forward tip of the needle cannula to a top surface of the limiter.

As used herein, the term "proximal" and derivatives thereof, shall mean the end of an item or direction away from a patient during use of the subject invention. The term "distal", and derivatives thereof, shall mean the end of an item or direction towards a patient during use of the subject invention. As used herein, the term "drug substance" and derivatives thereof, shall mean any substance that is intended for injection into a patient, including, by way of non-limiting example, drugs, vaccines, therapeutics, and the like. It will be obvious to a person of skill in the art, and from the disclosure provided herein, that the subject invention is not limited or otherwise defined by the type or class of substance administered using the inventive injection device.

An intradermal injection device constructed in accordance with embodiments of the present invention includes a syringe defining a reservoir in which a drug substance may be held, a needle cannula having a proximal end provided at a distal end of the syringe and in fluid communication with the reservoir and a distal needle tip. The inventive injection device also includes a movable limiter having a skin engaging surface with an aperture defined therethrough and through which the needle cannula may pass. The limiter is selectively moveable from a first retracted position in which an elongate portion ($d_1$) of the needle cannula is exposed and extends through the aperture and beyond the skin engaging surface, and a locked second extended position in which the limiter may not be moved from the second position back to the first position and in which the portion of the needle cannula exposed and extending through the aperture and beyond the skin engaging is limited to about 3 mm or less.

The present invention is also directed to a needle assembly for use in connection with a syringe for administering an intradermal injection. The inventive needle assembly may be coupled to a syringe and include a needle cannula having a proximal end provided at a distal end of the syringe and in fluid communication with the reservoir and a distal needle tip. The inventive needle assembly also includes a movable limiter having a skin engaging surface with an aperture defined therethrough and through which the needle cannula may pass. The limiter is selectively moveable from a first retracted position in which an elongate portion ($d_1$) of the needle cannula is exposed and extends through the aperture and beyond the skin engaging surface, and a lockable second extended position in which the limiter may not be moved back to the first position and in which the portion of the needle cannula exposed and extending through the aperture and beyond the skin engaging is limited to about 3 mm or less. The needle assembly may be coupled to the syringe using a luer-type connector, via a friction fit, using adhesive, or other now know or hereafter developed techniques for securing a needle cannula to a syringe.

Additionally, a method of intradermally injecting a mammal with a substance is provided including the steps of pressing a needle assembly of the invention in an orientation substantially perpendicular to the patient's skin such that the skin engaging surface of the limiter encounters the skin and prevents penetration of the needle cannula deeper than about 3 mm; maintaining the skin engaging surface on the skin and the orientation of the needle assembly; and injecting the substance under conditions and for a time sufficient to deliver the substance into the dermis layer of the skin.

The various features and advantages of this invention will become apparent to those skilled in the art from the following detailed description of the currently preferred embodiments. While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

DETAILED DESCRIPTION OF THE PREFERRED EMBODIMENTS

Figure 1:
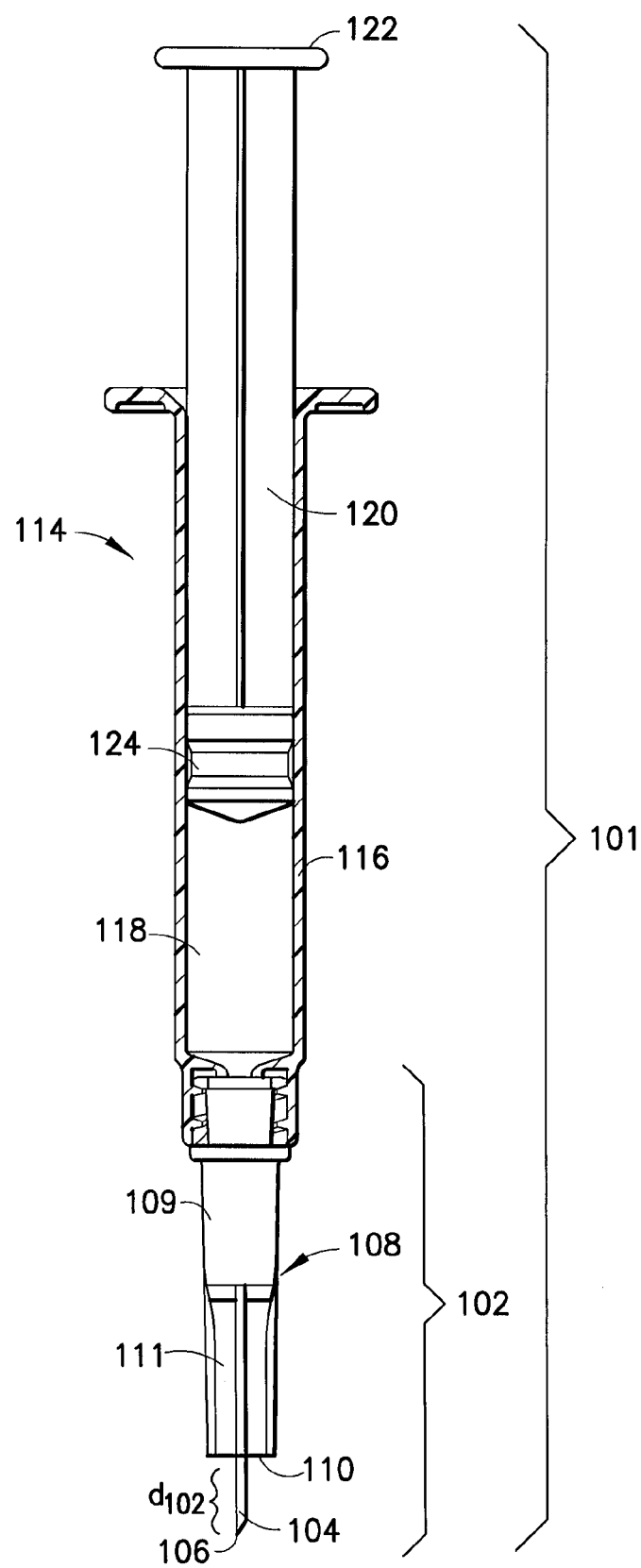
FIG. 1 shows a partial cross-sectional view of an intradermal injection device having a non-movable penetration limiter; intradermal
Figure 2:
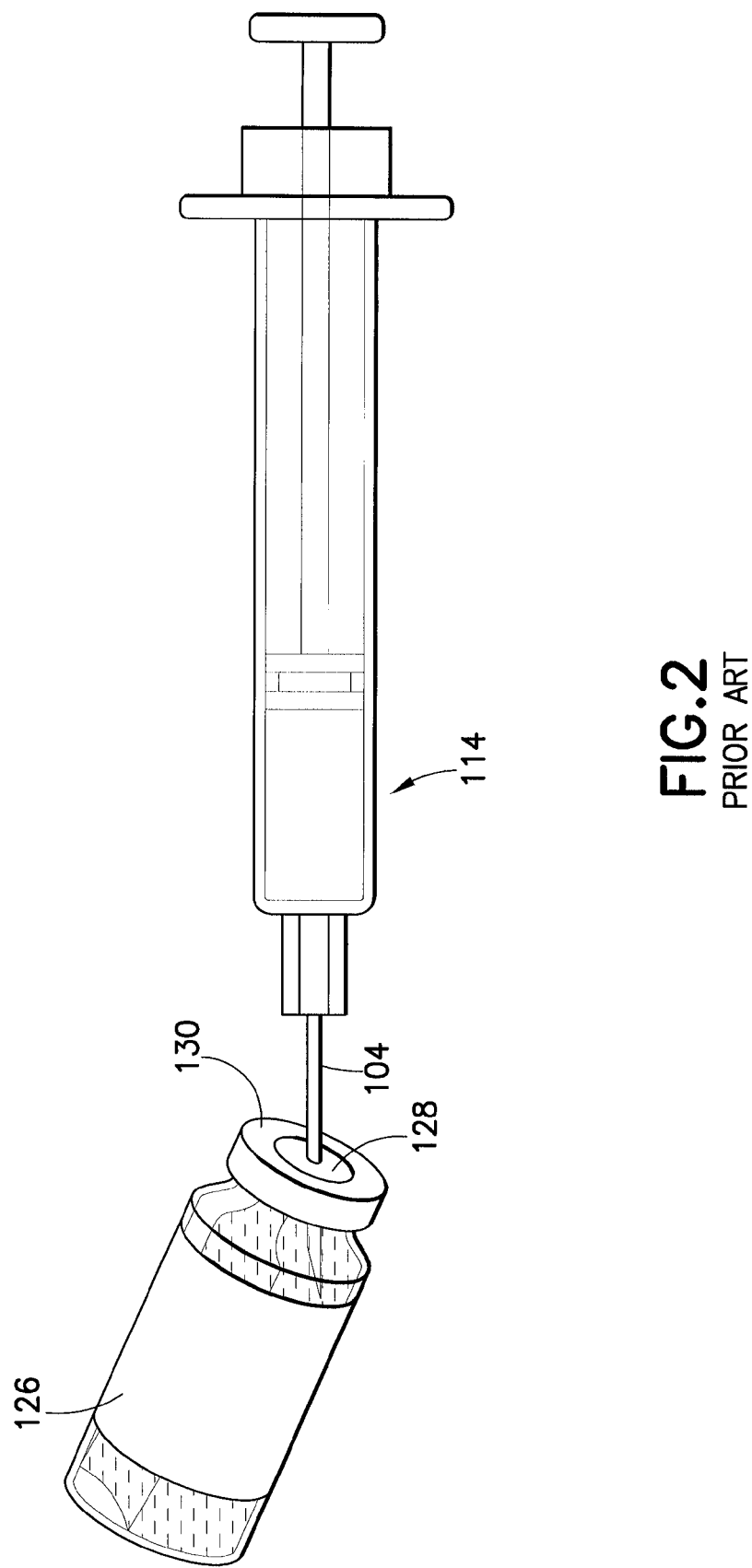
FIG. 2 shows a perspective view of a conventional syringe being filled from a multi-dose vial.
Figure 3:
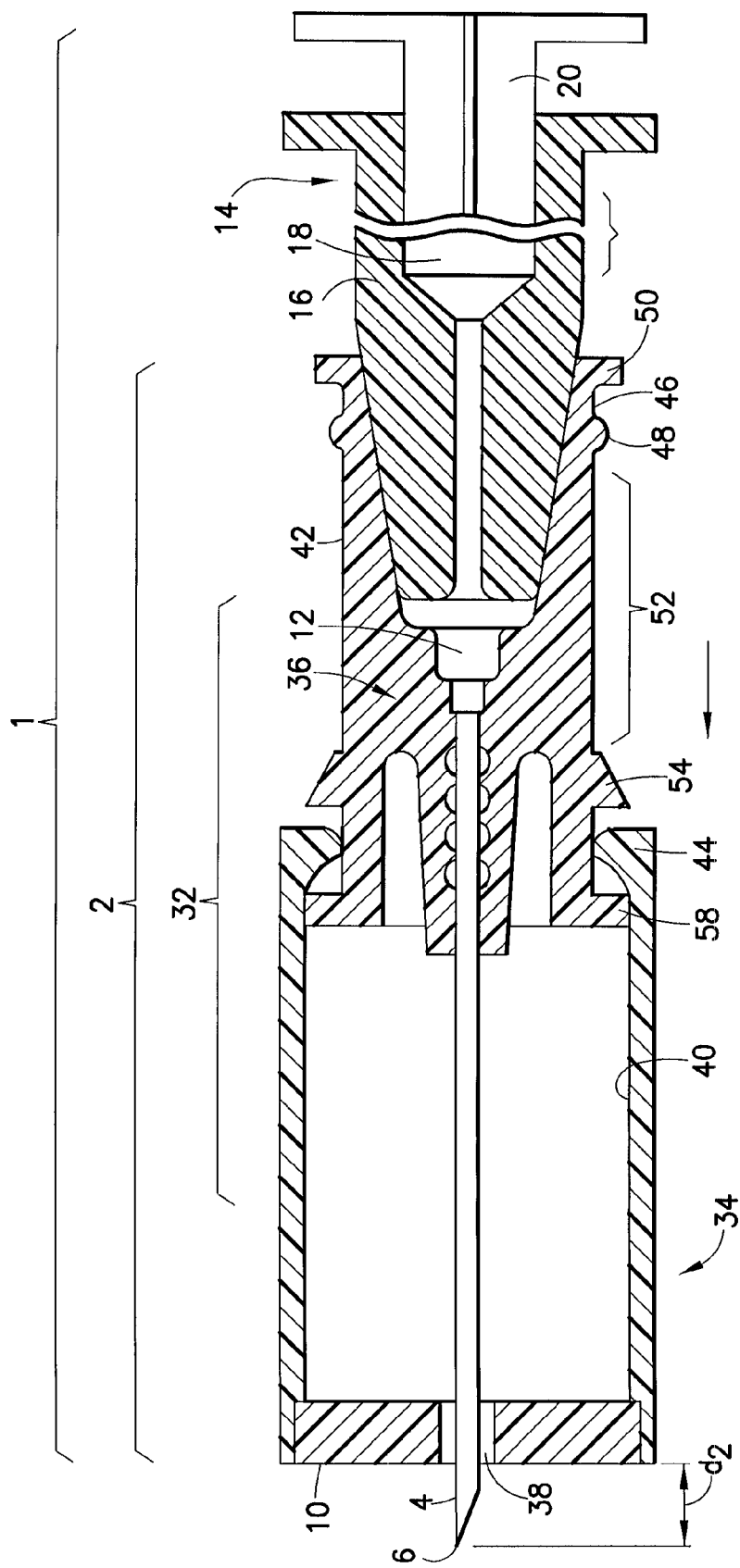
FIG. 3 shows an intradermal injection device having a needle assemble with a movable penetration limiter in the retracted position and constructed in accordance with an embodiment of the present invention.
Figure 4A:
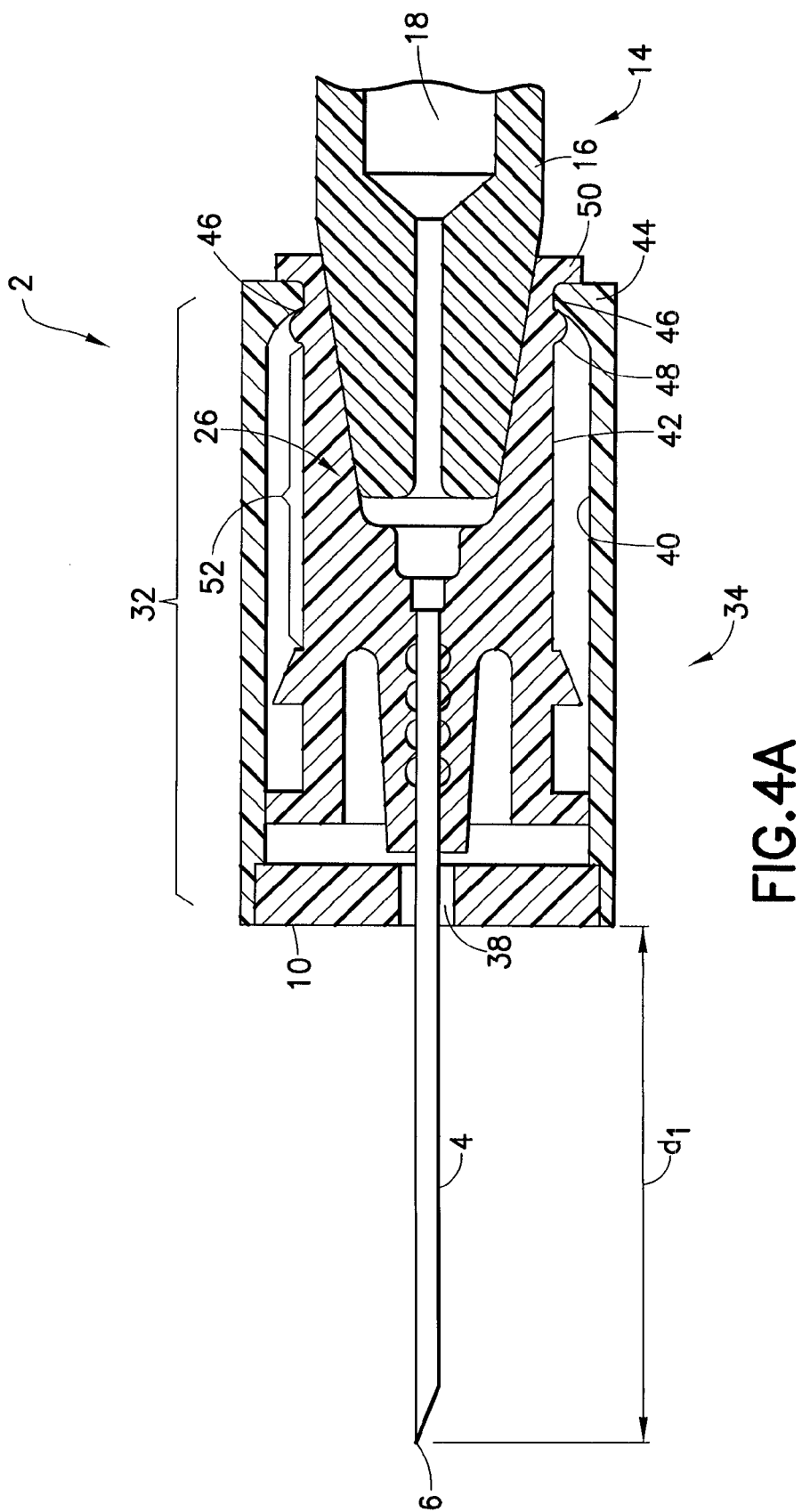
FIG. 4A shows a partial cross-sectional view of a needle assembly having a movable penetration limiter located in a retracted position and constructed in accordance with an embodiment of the present invention.
Figure 4B:
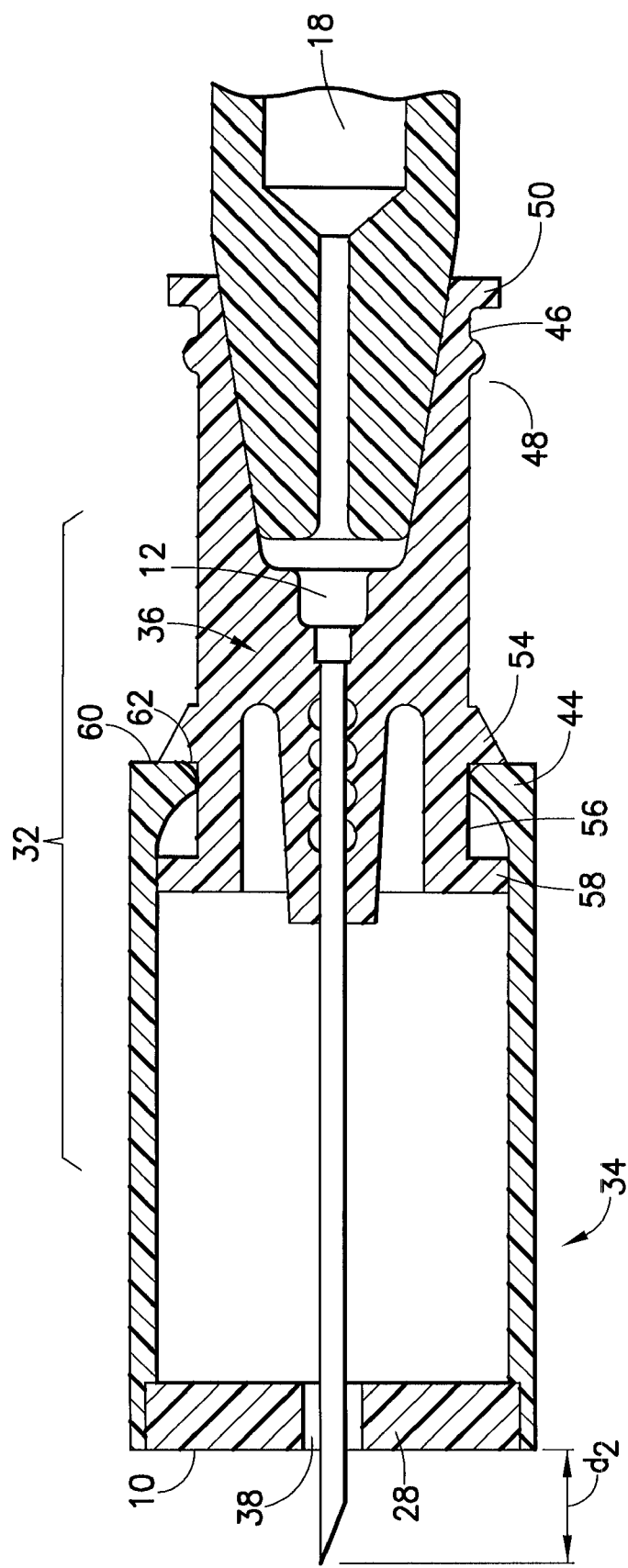
FIG. 4B shows the needle assembly of FIG. 4A with the movable penetration limiter in an extended position.

Referring next to the drawings in detail, in which like characters refer to like parts throughout the several views, FIGS. 3, 4A and 4B depict an intradermal injection device 2 and needle assembly 4, each constructed in accordance with embodiments of the present invention. The inventive injection device 1 includes a syringe 114 having a cylindrical body 116 that defines a reservoir 118 within which a drug substance may be contained and from which such substance may be expelled. A plunger 20 having a stopper 24 secured thereto is selectively movable within the reservoir 118, where movement in the proximal to distal direction will cause the drug substance to be expelled from the reservoir 118 through the needle cannula 4.

The inventive injection device 1 also includes a needle assembly 2 at the distal end of the body 116. The needle assembly 2 includes a needle cannula 4 supported by an inner support member 36 which is located at the distal end of the body 116. In the embodiment depicted in FIG. 3, inner support member 36 of the needle assembly 2 is secured to a hub 12 defined at that distal end of the body 116 in a manner known to those skilled in the art. For example, inner support member 36 may be secured using a friction fit, snap fit, suitable adhesive, luer connection, or other now known or hereafter developed means of securing a needle assembly to a syringe body. Alternatively, the needle cannula 4 may be secured directly to the body 116 via the hub 12 or other suitable structure that provides sufficient stability of connection between the needle cannula 4 and body 116 and that permits fluid communication between the reservoir 118 and needle cannula 4.

The needle assembly 2 further includes a limiter 32 comprised of an outer sheath 34 and the inner support member 36. In the embodiment depicted in FIG. 3, the inner support member 36 performs the function of a conventional hub. It is also possible to separately form a hub and an inner support member. However, for ease in construction, it is preferred that the hub and inner support member be formed unitarily. The outer sheath 34 has a generally flat skin engaging surface 10 defined at its distal end. The skin engaging surface 10 is preferably generally planar and continuous and provides for stable placement of the inventive injection device 1 against a patient's skin. The skin engaging surface 10 may, however, have alternate configurations. An aperture 38 is defined through the skin engaging surface 10 that is sized and shaped to permit the needle cannula 4 to pass freely therethrough when the outer sheath 34 is moved from the first position to the second position, as discussed in more detail below and elsewhere herein.

The outer sheath 34 is a generally tubular member that is selectively movable between a first retracted position, depicted in FIG. 4A, in which the a first predetermined length of the needle cannula 4 is exposed, and a locked second extended position, depicted in FIG. 4B, in which the limiter may not be moved back to the first position and in which a second predetermined length of the needle cannula 4 is exposed; the second predetermined length being shorter than the first predetermined length. When the sheath 34 is in the retracted position, as shown in FIG. 4A, the needle cannula 4 extends through the aperture 38 and the needle tip 6 is located a predetermined distance $d_1$ beyond the skin engaging surface 10; the predetermined distance preferably being in excess of about 5 mm. Preferably, $d_1$ is in the range of about 8 mm to about 15 mm, more preferably, $d_1$ is in the range of about 10 mm to about 13 mm. The length $d_1$ is sufficient to permit a user to insert the needle tip 6 into a conventional multi-use vial to withdraw a drug substance stored therein.

The outer sheath 34 is preferably in the first position depicted in FIG. 4A when it is desired to aspirate the syringe 14 with a drug substance from a multi-use vial. Once the desired dose is drawn into the reservoir 18 (by causing the plunger 120 and stopper 124 to move in a distal to proximal direction), the outer sheath 34 may be moved from the first position to the locked second position, depicted in FIG. 4B.

The sheath 34 is selectively movable on and along the support member 36 from a retracted position as illustrated in FIG. 4A, in which an elongate portion $d_1$, of the needle cannula 4, including the needle tip 6, is exposed through the aperture 38 and extends beyond the skin engaging surface 10, to a locked extended position as illustrated in FIG. 4B, in which a shorter portion $d_2$ of the needle cannula 4, including the needle tip 6, is exposed through the aperture 38 and extends beyond the skin engaging surface 10.

The inner support member 36 resides at least partially within the sheath 34 and is shown carrying the needle cannula 4 and being attached at a distal end of the syringe body 116. However, it is to be understood that other configurations are possible. For example, it is possible for the needle cannula 4 to be carried directly by the syringe body 116, either being secured directly to the syringe body 116 or being removably securable thereto. Additionally, the support member 36 may be formed unitarily with the syringe body 116 such that elements defined on the support member 36 as described below, will be formed on the syringe body 116. Each of these configurations is envisioned as within the scope of the invention, as are other configurations which will be apparent to those having ordinary skill in the art from the disclosure provided herein.

As discussed in further detail below, an inner surface 40 of the outer sheath 34 and an outer surface 42 of the inner support member 36 have cooperating parts which releasably secure the outer sheath 34 in the retracted position, and which lockingly secure the outer sheath 34 in the extended position.

Referring again to FIG. 4A, the outer sheath 34 may be releasably held in the retracted position by an inwardly directed projection 44 provided toward a proximal end of the sheath 34 and a corresponding recess 46 defined in the outer surface 42 of the support member 36 and bound by a retaining projection 48 and a proximal stop 50. The recess 46 is adapted to accept the projection 44 when the sheath 34 is in the retracted position. Movement of the sheath 34 in the proximal direction from the retracted position depicted in FIG. 4A is obstructed by interference between the projection 44 and proximal stop 50. Movement of the sheath 34 in the distal direction from the retracted position depicted in FIG. 4A is possible by applying sufficient force so that the projection 44 overcomes the retaining projection 48.

Upon application of a manual distal force to the sheath 34, the inwardly directed projection 44 moves out of the retaining recess 46 and moves distally beyond the retaining projection 48. The inwardly directed projection 44 then moves relatively along a cylindrical guide portion 52 of the support member 36.

Referring next to FIG. 4B, sheath 34 may be lockingly held in the extended position by complementary features defined on the sheath 34 and support member 36. A ramp 54, indent 56 and distal stop 58 are provided toward a distal end of the support member 36. The ramp 54 is wedge-shaped and is wider at its distal end than at its proximal end. The indent 56 is sized and shaped so as to accommodate the inwardly directed projection 44. The distal stop 58 prevents the inwardly directing projection 44 from moving distally beyond the indent 56, i.e., prevents the sheath 34 from being removed from the support member 36.

Once the sheath 34 is moved along the cylindrical guide portion 52, the inwardly directed projection 44 of the sheath 34 slides up and over the ramp 54 into the indent 56. When the sheath 34 is positioned as shown in FIG. 4B, with the inwardly directed projection 44 abutting the ramp 54, the needle tip 6 extends beyond the skin engaging surface 10 a distance ranging from approximately 0.5 to 3 mm. Preferably, the length the needle tip 6 extends beyond the skin engaging surface is sufficient to limit penetration of the needle cannula into the dermis, to a depth of 3 mm or less. More preferably, the length ranges from about 1 mm to about 2 mm.

Once the sheath 34 is in the extended position, the inventive intradermal device 1 is ready for use in administering an intradermal injection. Under normal conditions of use, pressure on the skin engaging surface 10 during an intradermal injection will move the inwardly directed projection 44 proximally in the indent 56 until a proximal edge 60 of the inwardly directed projection 44 abuts a distal edge 62 of the ramp 54.

The sheath 34, although preferably rigid, possesses sufficient elasticity to permit sufficient expansion to slide over the retaining projection 48 and/or the ramp 54 without damage to the sheath 34. Alternatively, or additionally, the support member 36 will possess sufficient flexibility to yield sufficiently to allow a substantially rigid sheath 34 to move beyond the retaining projection 48 and/or the ramp 54. However, the flexibility of the sheath 34 and/or support member 36 will not permit proximal movement of the sheath 34 from the extended position to the retracted position when exposed to forces normally associated with the use of injection devices.

In a further aspect of the invention, the inwardly directed projection 44 and the ramp 54 are configured so that when the sheath 34 is moved distally from the retracted position into the extended position, the inwardly directed projection 44 will snap past the end of the ramp 54, making an audible sound to provide an audible indication that the sheath 34 is in the extended position.

In a preferred embodiment of the present invention, all components of the intradermal device 2 will be made from moldable plastic materials such as, for example, polymeric plastics such as polypropylene, polycarbonate, and the like (except for the needle cannula 4 which is preferably made from steel). This construction allows for the syringe body 16 and the inner sheath 34 to be unitarily formed from a single moldable plastic. This is especially helpful in ease of assembly as well as reducing costs of manufacture.

The needle assembly 2 of the present invention may be supplied as an add-on to conventional drug delivery devices, i.e., glass or plastic syringes. In that case, the needle assembly 2 may be attached to a conventional drug delivery device, such as a syringe at the point of use. Alternatively, the needle assembly 2 may be provided with a syringe 14, thus comprising an intradermal device 1 in accordance with embodiments of the present invention. Generally, the intradermal device 1 will be provided with a protective packaging to maintain the integrity of the unit and/or sterility thereof. The intradermal device 1 may further be provided with a protective cap to cover the needle tip prior to use thereof.

In use, a health care professional administering the intradermal injection will unwrap the protective packaging from the needle assembly 2 (if provided as a separate component) or injection device 1. If necessary, the injection device 1 can be filled with the drug substance at this time, using methods that are conventional and known in the art. The health care professional will then manually slide the sheath 34 of the limiter 32 from the retracted position (see, e.g., FIG. 4A) to the extended position (see, e.g., FIG. 4B) in preparation for administration of the intradermal injection. Administration will typically involve pressing the skin engaging surface 10 of the limiter 32 substantially perpendicular to a surface of the patient's skin. The health care professional will maintain this orientation so as to maintain the needle in a position substantially perpendicular with the skin surface. The drug substance will then be injected using the plunger or other device conventionally used to deliver a drug substance. The injection will continue for a period of time determined by one having skill in the art based on the particular substance being administered as well as the dosage volume. Upon completion of the injection, the health care professional withdraws the needle cannula 4 from the patient's skin and disposed of the used injection device 1 in a suitable container.

Although the subject invention is well-suited for filling at point-of-use, it can be pre-filled. Optionally, for a prefilled device, a protective cap (not shown) may be provided for covering the needle before use, with the cap being positioned over the needle tip 6 and skin engaging surface 10. Preferably, the cap is formed from an elastomeric material or thermoplastic elastomer that allows for the forward tip 6 to penetrate the cap and thus be sealed thereby 34. Accordingly, the cap, by sealing the needle cannula 4, seals the reservoir and prevents the substance therein from leaking into the needle cannula 4 prior to administration of the intradermal injection. Such a cap also provides a certain degree of sterility for the needle tip 6 and maintains its sharpness.

Additionally, a shield member may also be provided for covering the needle tip 6 after use of the inventive injection device 1. Such a shield may be provided as part of the outer sheath 34, or as a component separate therefrom. Alternatively, the shield may be provided by the sheath 34 and support member 36, such as, for example, by providing additional complementary and interacting features on each part. Such features permitting further movement of the sheath 34 from the extended position to a shielding position in which the needle tip 6 is completely enclosed within the sheath 34, and the sheath 34 is lockingly secured to the support member 36 in the shielding position in another alternative embodiment, a needle shield may be hingedly attached to a part of the needle assembly 2 or syringe 14. Other equivalent structures may also be used for this purpose.

While the invention has been described in relation to the preferred embodiments with several examples, it will be understood by those skilled in the art that various changes may be made without deviating from the spirit and scope of the invention as defined in the appended claims.

What is claimed is:

1. A method of making an intradermal administration comprising:

providing a needle assembly having a needle cannula having a needle tip, a limiter surrounding said needle cannula and having a skin engaging surface, accessing a medication vial containing a substance with said needle cannula while said limiter is in a first position in which an elongate portion of said needle cannula is exposed from about 5 mm to about 15 mm, thereby allowing the needle tip to fully enter the medication vial;

moving said limiter to a locked second position in which said limiter is not movable from said second position to said first position and in which said needle tip extends beyond said skin engaging surface a pre-selected distance of about 3 mm or less; and administering said substance through said needle cannula.

2. The method of claim 1, wherein said needle tip extends beyond said skin engaging surface a distance of about 0.5 mm to about 3 mm.

3. The method of claim 2, wherein said needle tip extends beyond said skin engaging surface a distance of about 1 to about 2 mm.

4. The method of claim 1, wherein said skin engaging surface is substantially planar.

5. The method of claim 1, wherein said limiter comprises:
a support member arranged about said needle cannula; and
an outer sheath arranged about said support member and selectively slidable with respect thereto from said first position to said second position.

6. The method of claim 5, wherein said limiter further comprises first means for releasably holding said outer sheath in said first position, and second means for lockingly holding said sheath in said second position.

7. The method of claim 6, wherein said first means comprises a retaining projection and stop member on said support member and a projection on said sheath.

8. The method of claim 6, wherein said second means comprises a proximal stop arranged toward a proximal end of said support member, said proximal stop being configured so as to prevent further proximal movement of said inwardly directed projection from said retracted position.

9. The method of claim 8, further comprising a recess proximal said retaining projection for accommodating said inwardly directed projection of said sheath when said limiter is in said retracted position.

10. The method of claim 5, wherein said support member includes a distal stop toward a distal end of said support member, a ramp proximal to said outwardly directed projection and an indent interposed therebetween, wherein said inwardly directed projection resides within said indent when said limiter is in said extended position.

11. The method of claim 10, wherein said inwardly directed projection includes a proximal edge, said ramp includes a distal edge, whereby said proximal edge is in abutting contact with said distal edge when said limiter is in said extended position.

12. The method of claim 5, further comprising
attaching a hub, which is disposed about said needle cannula, to a container for delivering a substance, thereby placing the container in fluid communication with the needle cannula.

13. The method of claim 12, wherein said hub and said support member are unitarily formed.

14. A method of making an intradermal administration comprising:
providing a needle cannula having a needle tip, a limiter surrounding said needle cannula and having a skin engaging surface, a container adapted to contain a substance for intradermal injection, said container being in fluid communication with said needle cannula;

accessing a medication vial containing the substance with the needle cannula while said limiter is in a first position in which an elongate portion of said needle cannula is exposed from about 5 mm to about 15 mm;

filling the container with the substance;

moving said limiter to a locked second position in which said limiter is not movable from said second position to said first position and in which said needle tip extends beyond said skin engaging surface a pre-selected distance of about 3 mm or less;

administering said substance through said needle cannula.

15. The method of claim 14, wherein said needle tip extends beyond said skin engaging surface a distance of about 0.5 mm to about 3 mm.

16. The method of claim 14, wherein said needle tip extends beyond said skin engaging surface a distance of about 0.5 mm to about 2 mm.

17. The method of claim 16, wherein said needle tip extends beyond said skin engaging surface a distance of about 1 to about 2 mm.

18. The method of claim 14, wherein said skin engaging surface is substantially planar.

19. The method of claim 14, wherein said limiter comprises:
a support member about said needle cannula; and
an outer sheath arranged about said support member and selectively slidable with respect thereto from said first position to said second position.

20. The method of claim 19, wherein said limiter further comprises first means for releasably holding said outer sheath in said first position, and second means for lockingly holding said sheath in said second position.

21. The method of claim 20, wherein said first means comprises a retaining projection and stop member on said support member and a projection on said sheath.

22. The method of claim 20, wherein said second means comprises a proximal stop arranged toward a proximal end of said support member, said proximal stop being configured so as to prevent further proximal movement of said inwardly directed projection from said retracted position.

23. The method of claim 22, further comprising a recess proximal said retaining projection for accommodating said inwardly directed projection of said sheath when said limiter is in said retracted position.

24. The method of claim 19, wherein said support member includes a distal stop toward a distal end of said support member, a ramp proximal to said outwardly directed projection and an indent interposed therebetween, wherein said inwardly directed projection resides within said indent when said limiter is in said extended position.

25. The method of claim 24, wherein said inwardly directed projection includes a proximal edge, said ramp includes a distal edge, whereby said proximal edge is in abutting contact with said distal edge when said limiter is in said extended position.

26. The method of claim 19, further comprising:
attaching a hub, which is disposed about said needle cannula, to a container for delivering a substance, thereby placing the container in fluid communication with the needle cannula.

27. The method of claim 26, wherein said hub and said support member are unitarily formed.

* * * * *